United States Patent
Noble (12) 
(10) Patent No.: US 6,575,925 B1
(45) Date of Patent: Jun. 10, 2003

(54) FINGER SPLINT

(75) Inventor: Terrance O. Noble, Burnsville, MN (US)

(73) Assignee: Apothecary Products, Inc., Burnsville, MN (US)

( * ) Notice: Subject to any disclaimer, the term of this patent is extended or adjusted under 35 U.S.C. 154(b) by 0 days.

(21) Appl. No.: 09/573,858

(22) Filed: May 18, 2000

(51) Int. Cl.[7] .................................................. A61F 5/00
(52) U.S. Cl. .......................................... 602/20; 602/23
(58) Field of Search ........................... 602/20, 21, 22; 128/877, 878, 879

(56) References Cited

U.S. PATENT DOCUMENTS

| | | | | |
|---|---|---|---|---|
| 1,375,690 A | * | 4/1921 | George | 602/22 |
| 2,548,378 A | * | 4/1951 | Kleinfeld | 602/22 |
| 4,644,941 A | * | 2/1987 | Ogle | 602/22 |
| 4,657,000 A | | 4/1987 | Hepburn | |
| 5,101,812 A | * | 4/1992 | Wang | 602/22 |
| 5,147,285 A | * | 9/1992 | Buxton | 602/22 |
| 5,267,945 A | | 12/1993 | Doctor et al. | |
| 5,681,269 A | * | 10/1997 | Basaj | 602/5 |

OTHER PUBLICATIONS

*Apothecary Products, Inc.: The Pharmacy Buyer's Guide to Drug Specialties*, Sep. 1998, pp. 65–70.

\* cited by examiner

*Primary Examiner*—Michael A. Brown
(74) *Attorney, Agent, or Firm*—Merchant & Gould P.C.

(57) ABSTRACT

The disclosure provides a finger splint comprising a supporting shell and at least one securing member affixed to the supporting shell. In one embodiment, the securing member is affixed to the supporting shell using an adhesive. In another embodiment, the supporting shell further comprises a retaining member extending from the supporting shell wherein the retaining member is configured to anchor the securing member to the supporting shell. In a preferred embodiment, the securing member is constructed from a hook and loop material such as VELCRO®.

13 Claims, 7 Drawing Sheets

FINGER SPLINT

FIELD OF THE INVENTION

This invention relates to a finger splint, more particularly to a finger splint which includes a securing member for fastening the splint onto a finger.

BACKGROUND OF THE INVENTION

A splint is a device used for holding a part of the body stable, typically to protect a wounded body part from further damage and to facilitate healing.

Splints can be used to treat a variety of injuries, including injuries to fingers such as strains, sprains, fractures and breaks. Essentially, a splint can be any a rigid material such as a stick or board used to immobilize a body part. In some cases, an injured body part can be taped to an uninjured body part to prevent movement. For example, an injured finger can be taped directly to an adjacent finger. Commercial splints are also available.

The splint typically secured to the injured body part (typically at positions located above and below the injury, rather than directly over the injury) body using ties, or tape.

One benefit associated with using a splint, versus a plaster or fiberglass cast, for immobilizing an injured finger, is the ability to adjust, remove and replace the splint as desired. For example, a splint may be applied to a fresh injury and, as swelling subsides, the splint may be adjusted to maintain a snug fit. Additionally, as an injury heals, a splint may be removed for therapy. Furthermore, a patient may want to remove a splint, for example, during bathing.

However, typical methods for securing the splint to the injured body part are cumbersome to remove and replace, and, in the case of tape, leave a sticky residue. Therefore, a splint with securing means that are easily applied, removed and replaced, particularly by the injured patient, is desirable.

SUMMARY

The invention provides a finger splint which includes a securing member that is easily applied, removed and replaced.

The finger splint includes a supporting shell and a securing member affixed to said supporting shell. The securing member may be affixed to the supporting shell by an adhesive or may be anchored to the supporting shell by a retaining member. Preferably, the securing member is constructed from a hook and loop closure material such as VELCRO®.

DETAILED DESCRIPTION

This invention relates to a finger splint, more particularly to a finger splint which includes a securing member for fastening the splint onto a finger. As used herein, the term "finger" refers to the terminating members of the hand, including the thumb.

Figure 1A:
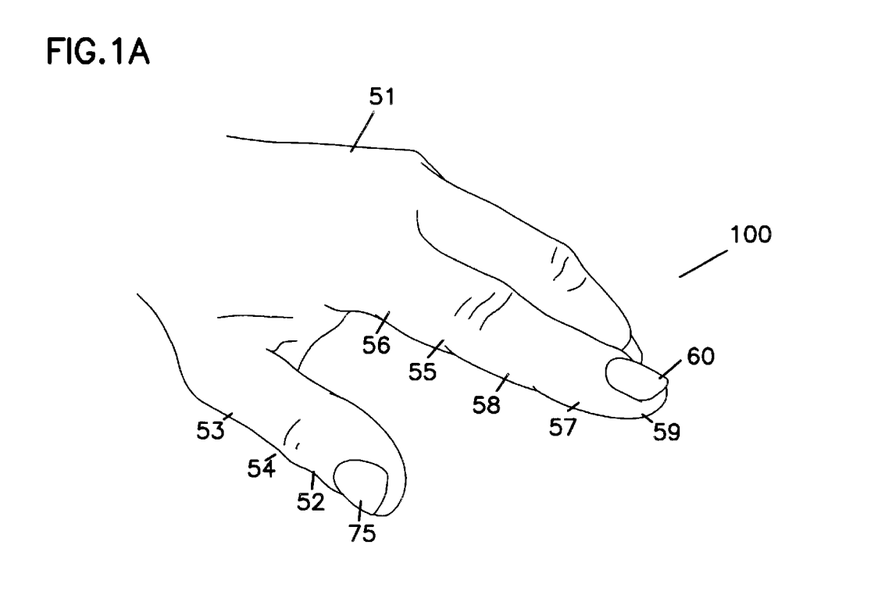
FIGS. 1a and 1b are illustrations of a hand.
Figure 1B:
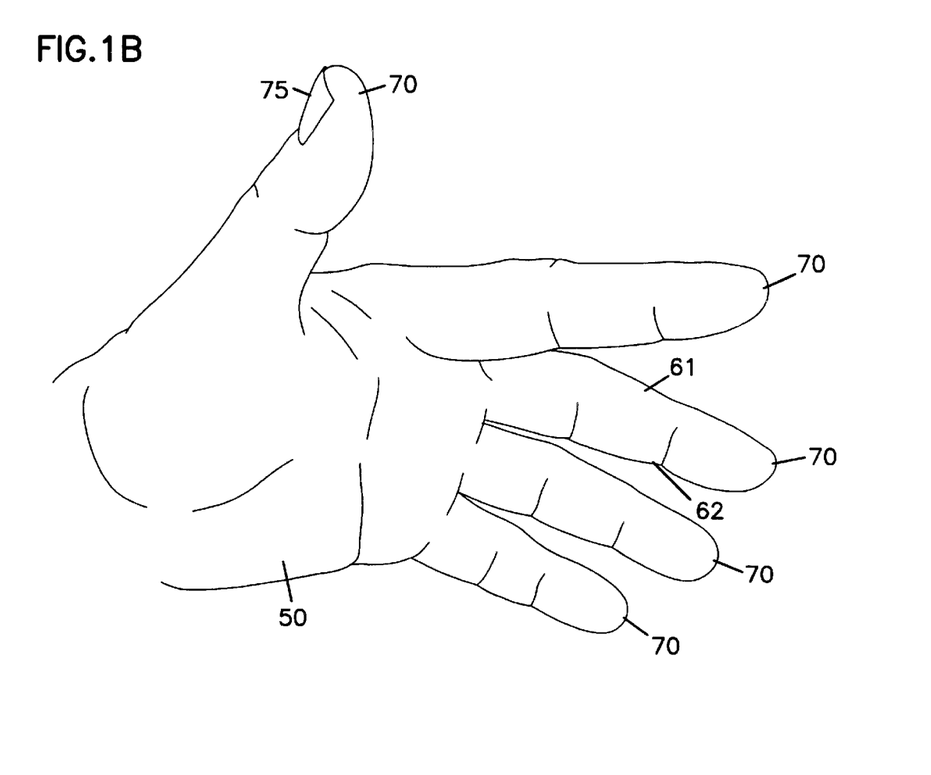

Prior to discussing the splint, a discussion of the hand will be provided to facilitate an understanding of the invention. An illustration of a hand 100 is shown in FIGS. 1a and 1b. A normal human hand 100 has a palm surface 50 and a dorsal surface 51 and includes five digits 70 (four fingers and a thumb). Each finger has a lateral surface 62 and a medial surface 61. The fingers each include three bones or phalanges, the proximal 56, middle 58 and distal 59 phalanges. The thumb includes two bones or phalanges, the proximal 53 and distal 52 phalanges. Between the middle 58 and distal 59 phalanx of the finger is a distal joint 57 and between the proximal 57 and middle 58 phalanx of the finger is a proximal joint 55. Between the proximal 53 and distal 52 phalanx of the thumb is a thumb joint 54.

Figure 2A:
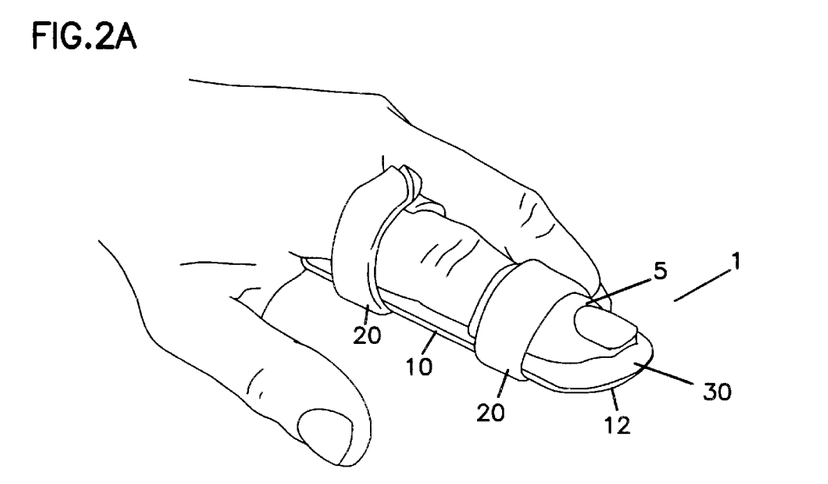
FIGS. 2a and 2b show a spoon splint and securing member according to the invention.
Figure 2B:
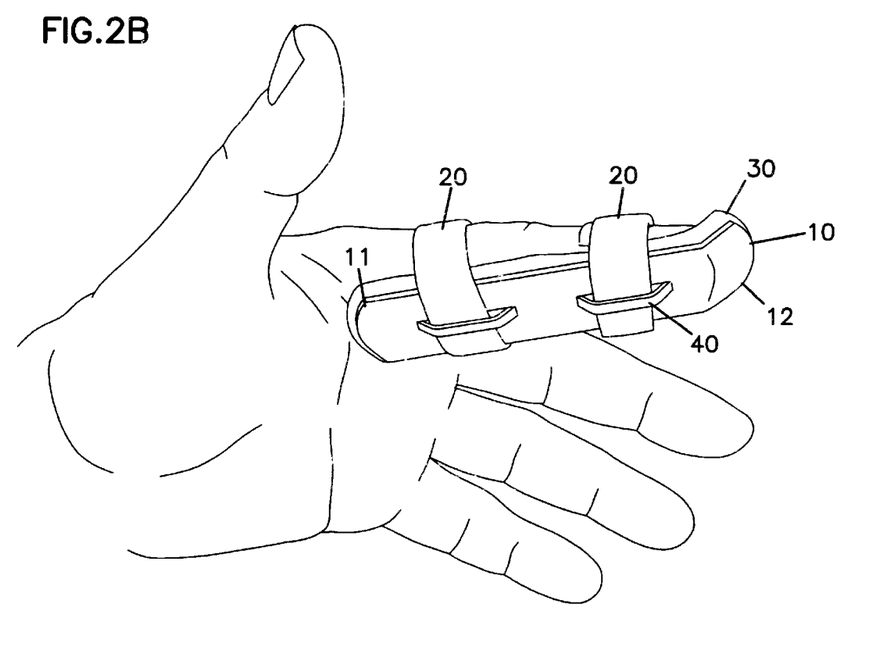

Referring to FIGS. 2a and 2b, the splint 1 generally includes a shell 10 and at least one securing member 20. Typically, the splint 1 includes an elongate shell 10 constructed from a supportive material, such as a metal, plastic, cardboard, wood or foam, that is designed to extend past at least one joint adjacent the injury.

The supporting shell 10 can be constructed from materials such as malleable aluminum, molded plastic, open cell foam and closed cell foam. Generally, open cell form is more compliant than closed cell foam. The shell 10 may also include a padding layer 30 constructed of a resilient material, such as mesh or knit fabric, for example gauze; nonwoven fibers, for example, cotton fibers; or foam, such as open cell foam, for example, polyurethane foam. Typically, the padding 30 is positioned to lie adjacent to the injured finger 5 when in use. The padding 30 may optionally be covered, for example, with a vinyl covering (not shown).

According to the invention, the splint 1 also includes at least one securing member 20. The securing member 20 is configured to selectively, adjustably, and releasably secure the splint 1 to a patient's finger, for example, the injured finger or an adjacent finger. Generally, the securing member 20 extends laterally from the supporting shell 10 of the splint and is capable of encircling the shell 10 and the patient's finger. Preferably, the securing member is constructed from a hook and loop closure material such as VELCRO®.

In one embodiment, the securing member 20 can be affixed to the supporting shell 10, for example, by an adhesive or by a welding process. In an alternate embodiment, a retaining member 40 anchors the securing member 20 to the supporting shell 10.

In one embodiment, the retaining member 40 is formed integrally with the supporting shell 10. As used herein, the term "integral" refers to a retaining member 40 that is formed as a single unit with the supporting shell 10, e.g., as part of a single molding process or through a process such as pressing or punching the retaining member 40 out of the supporting shell 10. Alternately, the retaining member 40 can be affixed to the supporting shell 10, for example, by an adhesive or by welding. The retaining member 40 defines a passage through which the securing member 20 extends. The passage can be closed, as shown in FIGS. 2a and 2b, or open on one end, as shown in FIGS. 3a and 3b.

Various shell 10 configurations are known, for example, spoons, cots, four sided finger protectors, baseballs, and ventilated open nail finger protectors. These shell 10 configurations will be described in more detail below.

In a spoon configuration, shown in FIGS. 2a and 2b, the shell 10 is constructed as an elongate article having a proximal end 11 that is positioned to support the proximal phalanx 56 of the finger during use and a distal end 12 that is positioned to support the distal phalanx 59 during use. In the spoon configuration, the distal end 12 of the shell 10 curves around the fingertip to protect the tip of the finger during use. In a spoon configuration, the splint 1 preferably includes a plurality of securing members 20. Preferably, a first securing member 20 is configured to encircle the proximal phalanx 56 of the finger and a second securing member 20 is configured to encircle the distal phalanx 59 or distal joint 57 of the finger. The retaining member 40 is positioned to keep the securing member 20 at the desired location.

Figure 3A:
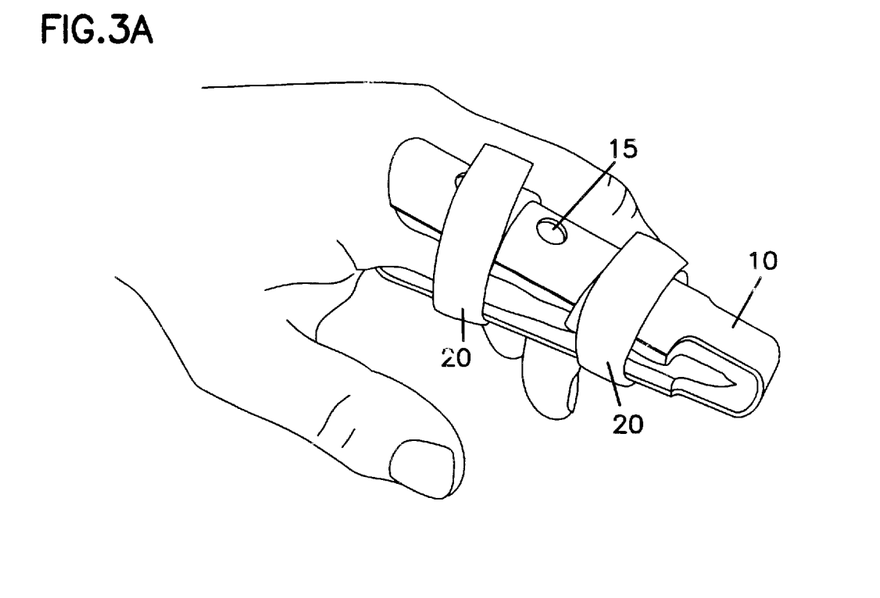
FIGS. 3a and 3b show a cot splint and securing member according to the invention.
Figure 3B:
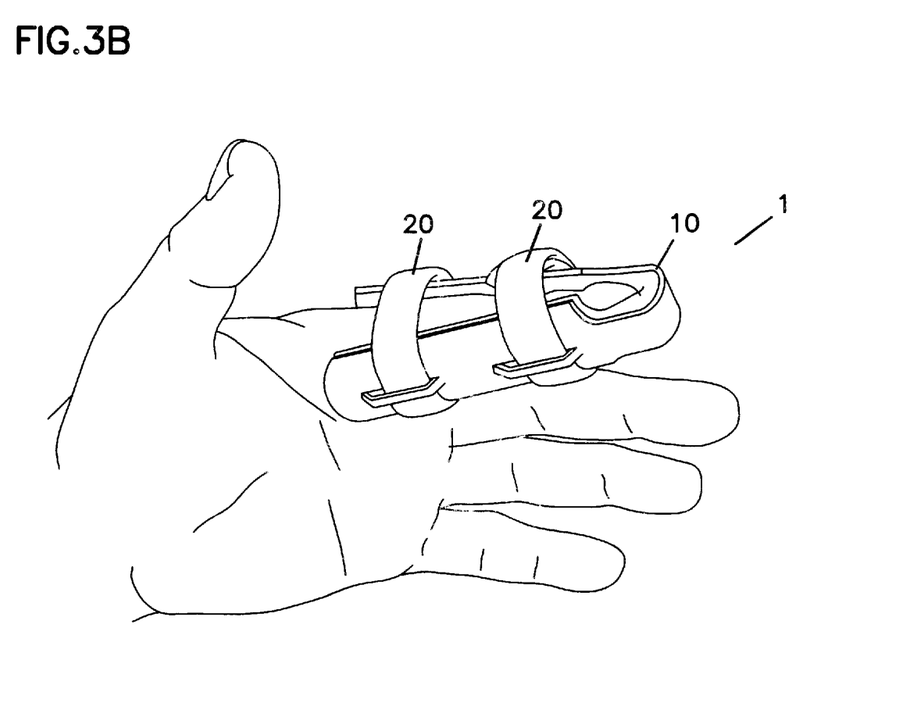

A "cot" configuration, shown in FIGS. 3a and 3b, is formed from an elongate unitary shell 10 that is folded over the tip of the finger to cover both the palm 50 and dorsal 51 surface of the finger. The "cot" configuration provides additional stabilization and protection as compared to the spoon configuration. Preferably, the shell 10 in the cot configuration defines at least one aperture 15 to increase ventilation. As in the spoon configuration, the elongate unitary shell 10 of the cot configuration preferably includes a plurality of securing members 20. Preferably, a first securing member 20 is configured to encircle the proximal phalanx 56 of the finger and a second securing member 20 is configured to encircle the distal phalanx 59 or distal joint 57 of the finger. Again, the retaining member 40 is positioned to keep the securing member 20 at the desired location.

Figure 4A:
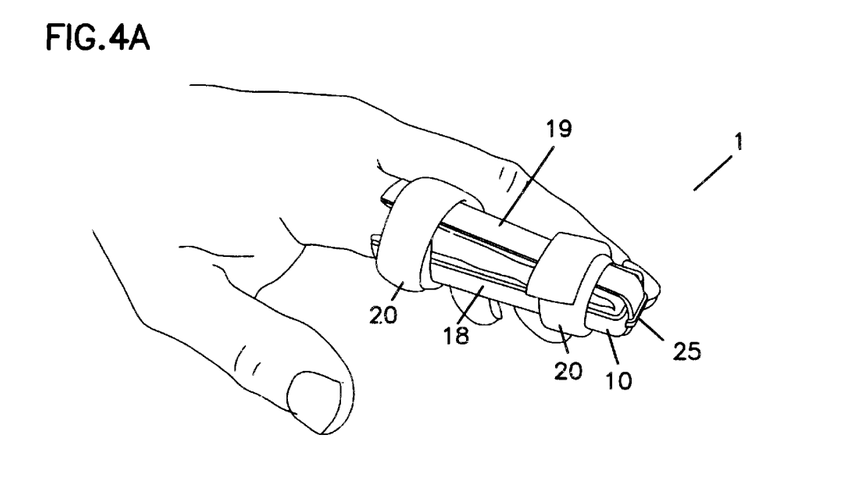
FIGS. 4a and 4b show a four sided finger protector splint and securing member according to the invention.
Figure 4B:
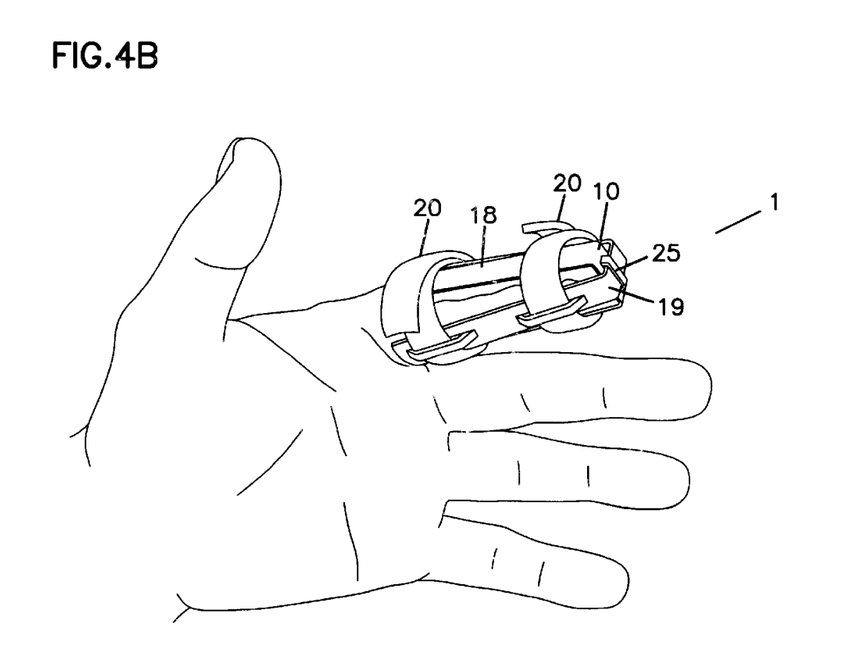

A "four sided finger protector" is shown in FIGS. 4a and 4b. The four sided finger protector configuration, provides even more support and protection than the "cot" configuration. The shell 10 of the "four sided finger protector" is constructed using a first 18 and second 19 elongate band. The first elongate band is formed form a unitary band 18 that is folded over the tip of the finger to extend along both the palm 50 and dorsal 51 surfaces of the finger. The second elongate band 19 is formed from a unitary band 19 that is folded over the tip of the finger to extend along both the lateral 62 and medial 61 surfaces of the finger. The first 18 and second 19 elongate bands intersect as they fold over the tip of the finger. Preferably, the first 18 and second 19 elongate bands are attached to one another at this intersection. In one embodiment, a keeper 25 projects outwardly from one of the bands (either the first 18 or second 19 band) to encircle the other band. The four sided finger protector splint 1 preferably includes a plurality of securing members 20. Preferably, a first securing member 20 is configured to encircle the proximal phalanx 56 of the finger and a second securing member 20 is configured to encircle the distal phalanx 59 or distal joint 57 of the finger. The retaining member 40 is positioned to keep the securing member 20 at the desired location.

Figure 5A:
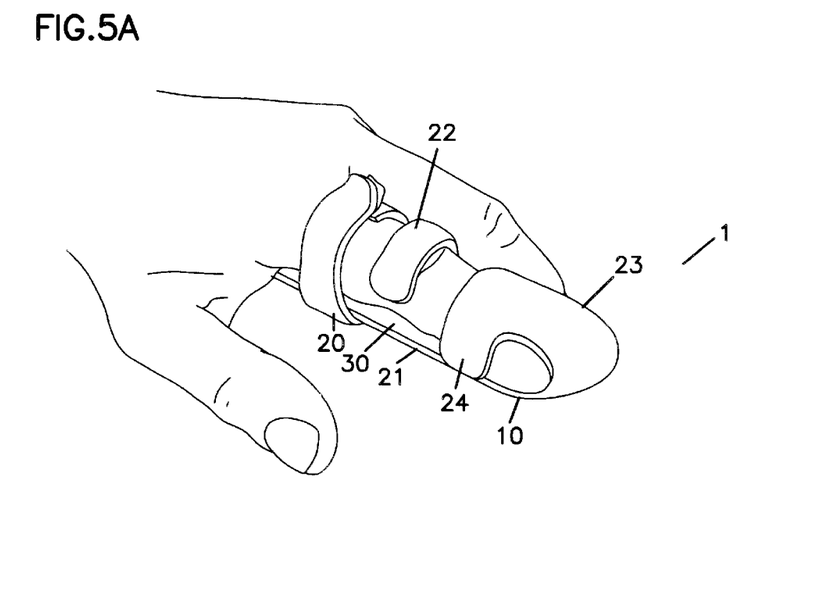
FIGS. 5a and 5b show a baseball splint and securing member according to the invention.
Figure 5B:
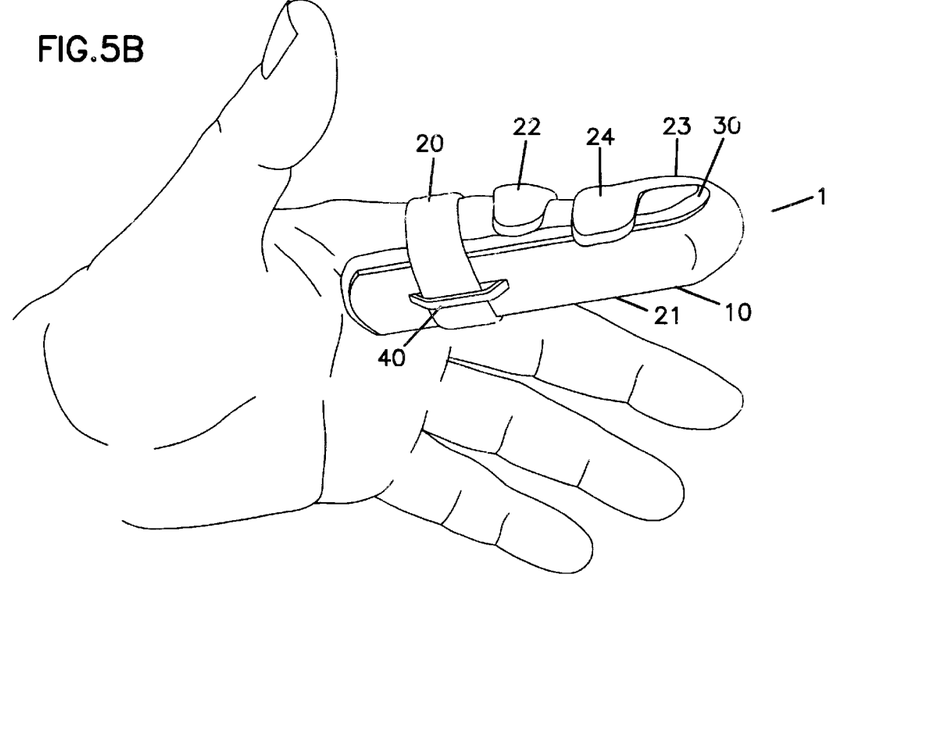

A "baseball" configuration, shown in FIGS. 5a and 5b, is typically used to stabilize, immobilize and protect distal phalanx fractures. The supporting shell 10 of the baseball splint 1 includes an elongate member 21 which is configured to extend along the palm surface of the finger, fold over the tip of the finger and extend to cover the dorsal surface of the distal phalanx 59, optionally covering the distal joint 57 of the finger. The element of the shell 10 that covers the dorsal surface of the distal phalanx of the finger is hereinafter referred to as the "extender" 23. Preferably, the extender 23 includes a first 24 and a second (not shown) tabs which extend laterally and medially from the extender 23 and can be manipulated to encircle the distal phalanx 59 and/or distal joint 57 of the finger. Preferably, the supporting shell 10 also includes a lateral flange 22 which is configured to fold over and encircle the middle phalanx 58 of the finger, and optionally, either the proximal joint 55 and/or the distal joint 57. The baseball splint 1 preferably includes a single securing member 20 configured to encircle the proximal phalanx of the finger. One of skill in the art could envision a similar construction for immobilizing an injury to the distal phalanx of the thumb.

Figure 6A:
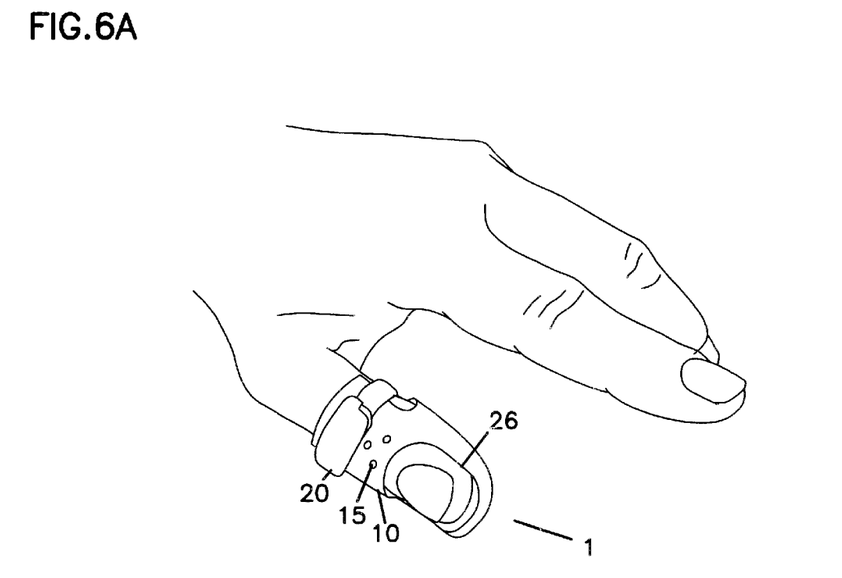
FIGS. 6a and 6b show a ventilated open nail finger protector and securing member according to the invention.
Figure 6B:
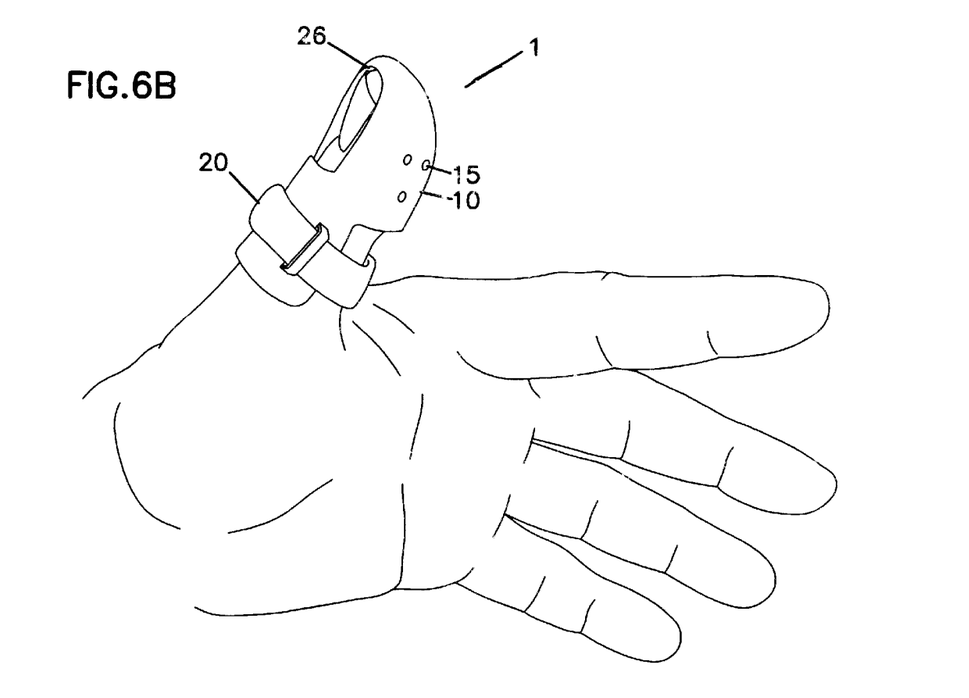

A "ventilated open nail finger protector" splint configuration is shown in FIGS. 6a and 6b. This configuration supports the distal phalanx and finger tip while allowing movement of the proximal joint. Although other materials can be used, the vented open nail finger protector shell 10 is preferably constructed as a unitary molded plastic device. The shell 10 of the ventilated open nail finger protector is configured to encompass the distal phalanx 59 or 52 of the finger. Preferably, the shell 10 defines an opening 26 through which the fingernail 75 of the patient is visible. Preferably the palm surface of the shell 10 is configured to extend only to cover distal phalanx 59, 52 of the finger. In contrast, the dorsal surface of the shell 10 is configured to extend past the distal joint 57 of the finger (and/or thumb joint 54). According to the invention, the ventilated open nail finger protector splint configuration also includes a securing member 20 that is configured to encircle the middle phalanx 58 of the finger or the proximal phalanx 53 of the thumb. The retaining member 40 is positioned to keep the securing member 20 at the desired location.

Figure 7:
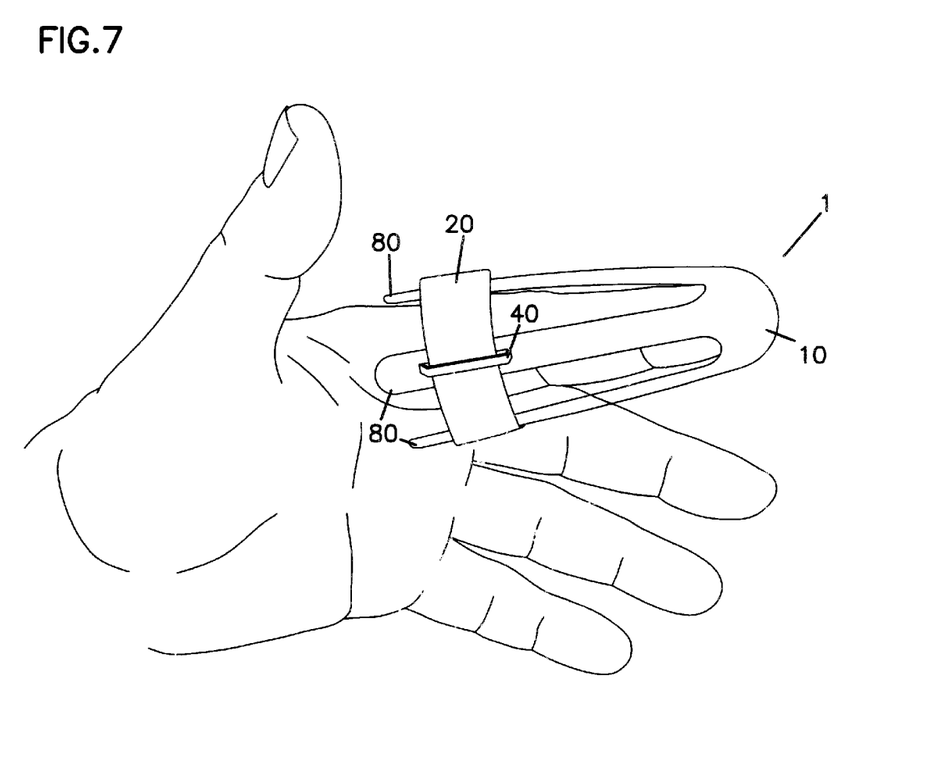
FIG. 7 shows a four pronged finger guard according to the invention.

A "four pronged finger guard" is shown in FIG. 7. Generally, the four pronged finger guard 1 comprises a unitary plastic shell 10 having a plurality of prongs 80 and at least one securing members 20. Preferably unitary plastic shell 10 comprises four prongs, with a first prong 80 configured to extend along the palm 50 surface of the finger, a second prong 80 configured to extend along a dorsal 51 surface of the finger, a third prong configured to extend along the lateral 62 surface of the finger and a fourth prong configured to extend along a medial 61 surface of the finger. Preferably, a first securing member 20 is configured to encircle the proximal phalanx 56 of the finger. If desired, a second securing member 20 can added, configured to encircle the distal phalanx 59 or distal joint 57 of the finger. The retaining member(s) 40 is(are) positioned to keep the securing member 20 at the desired location. If desired, the finger can be wrapped with a bandage prior to securing the four pronged finger guard to the finger.

Although the present invention has been described in relation to particular embodiments thereof, many other variations and other uses will become apparent to those of skill in the art. The invention is limited not by the specific disclosure herein, by only by the appended claims.

What is claimed is:

1. A finger splint constructed in a baseball configuration comprising:
    an elongate unitary shell configured to extend along a palm surface of a finger, said shell having distal and proximal ends, an extender at the distal end and a lateral flange between the distal and proximal ends, wherein said extender is configured to fold over a tip of the finger and to extend to cover a dorsal surface of a distal phalanx, or distal phalanx and distal joint, of the finger, the extender having first and second tabs configured to extend laterally and medially from the extender, said first and second tabs constructed of malleable material such that they can be manipulated to encircle the distal phalanx or distal phalanx and distal joint, of the finger, wherein said lateral flange extends laterally from the shell and is constructed of malleable material such that it can be folded over to encircle a middle phalanx of the finger, the middle phalanx and proximal joint of the finger or the middle phalanx and distal joint of the finger;

a securing member sized and configured to encircle a finger, the securing member comprising a hook and loop material; and a retaining member on the palm surface of the shell at the proximal end, wherein said retaining member defines a passage through which the securing member extends, the retaining member having distal and proximal ends corresponding to the distal and proximal ends of the shell, wherein the proximal end of the retaining member is connected to the shell and the distal end of the retaining member is free, such that the retaining member releasably attaches the securing member to the proximal end of the shell such that the securing member encircles the proximal phalanx of the finger.

2. The splint according to claim 1, wherein said retaining member is integral with said supporting shell.

3. The splint according to claim 1, wherein said retaining member is mounted on said supporting shell.

4. The splint according to claim 1, wherein said shell is constructed from a material selected from the group consisting of plastic, metal, cardboard, wood, fabric and foam.

5. The splint according to claim 1, wherein said shell further comprises a padding layer.

6. The splint according to claim 5, wherein said padding layer is constructed from a resilient material selected from the group consisting of knit material, woven material, non-woven material, and foam.

7. The finger splint according to claim 1, wherein said securing member is constructed from a hook and loop closure material.

8. The splint according to claim 1, wherein said elongate shell has a longitudinal axis extending from the proximal end to the distal end, and said retaining member is connected to the shell such that the retaining member extends along the longitudinal axis of the shell.

9. A finger splint for immobilizing an injured finger comprising:

a unitary supporting shell sized and configured to extend past at least one finger joint adjacent an injury, said shell having distal and proximal ends and a longitudinal axis extending from the proximal end to the distal end;

at least one securing member sized and configured to encircle a finger, the securing member comprising a hook and loop material; and at least one retaining member extending from the supporting shell, said retaining member having distal and proximal ends corresponding to the distal and proximal ends of the shell, wherein the proximal end of the retaining member is connected to the supporting shell and the distal end of the retaining member is free, wherein the retaining member is connected to the shell such that the retaining member extends along the longitudinal axis of the shell, the retaining member configured to removably attach said securing member to said supporting shell, said retaining member forming a passage through which the securing member extends, wherein each securing member is removably attached to the supporting shell by a single retaining member.

10. The splint according to claim 9, wherein said shell configuration is selected from the group consisting of spoon, cot, four sided finger protector, baseball and ventilated open nail finger protector.

11. The splint according to claim 9, wherein said supporting shell is constructed from material selected from the group consisting of plastic, metal, cardboard, wood, fabric and foam.

12. The splint according to claim 9, wherein said supporting shell further comprises a padding layer.

13. The splint according to claim 9, comprising two securing members and two retaining members, wherein the retaining members are connected to the shell in a tandem arrangement.

* * * * *